United States Patent [19]

Toso et al.

[11] Patent Number: 5,312,420

[45] Date of Patent: May 17, 1994

[54] SURGICAL APPARATUS FOR REMOVING FASTENERS

[75] Inventors: Kenneth E. Toso, Portchester, N.Y.; Michael Castro, Seymour, Conn.

[73] Assignee: United States Surgical Corporation, Norwalk, Conn.

[21] Appl. No.: 959,301

[22] Filed: Oct. 9, 1992

[51] Int. Cl.$^5$ .................................. A61B 17/06
[52] U.S. Cl. ............................. 606/138; 606/205; 606/206
[58] Field of Search ............. 606/138, 142, 151, 156, 606/205-208, 210-211; 81/302, 424, 427, 427.5; 227/901, 902

[56] References Cited

U.S. PATENT DOCUMENTS

| | | | |
|---|---|---|---|
| 1,832,879 | 11/1931 | Ruskin | 606/208 |
| 2,887,110 | 5/1959 | Roeschmann | 606/205 |
| 3,254,649 | 6/1966 | Wood | 606/205 |
| 3,283,557 | 11/1966 | Wood | 606/205 |
| 3,817,078 | 6/1974 | Reed et al. | 606/211 |
| 4,312,337 | 1/1982 | Donohue | 606/205 |
| 4,569,505 | 2/1986 | Braun | 254/28 |
| 4,586,503 | 5/1986 | Kirsch et al. | 606/138 |
| 4,685,460 | 8/1987 | Thornton | 606/205 |
| 5,015,252 | 5/1991 | Jones | 606/205 |
| 5,019,091 | 5/1991 | Porat et al. | 606/205 |
| 5,047,037 | 9/1991 | Brandfield | 606/138 |

FOREIGN PATENT DOCUMENTS 9307814 4/1993 World Int. Prop. O. .......... 606/205

Primary Examiner—Stephen C. Pellegrino
Assistant Examiner—M. Peffley

[57] ABSTRACT

A surgical apparatus for removing fasteners from the body includes a pair of fastener removing members which are configured and dimensioned to contact the legs of a fastener to be removed. The legs are then forced apart so as to caused the fastener legs to deform to a configuration suitable for removable from the body.

28 Claims, 4 Drawing Sheets

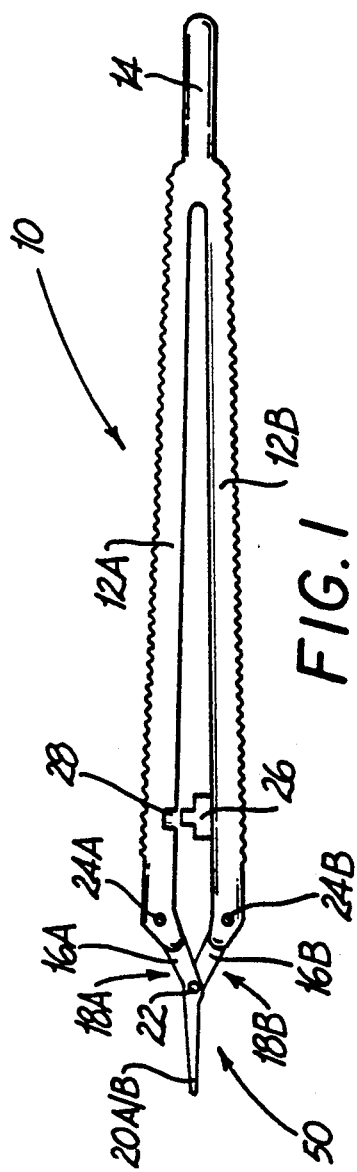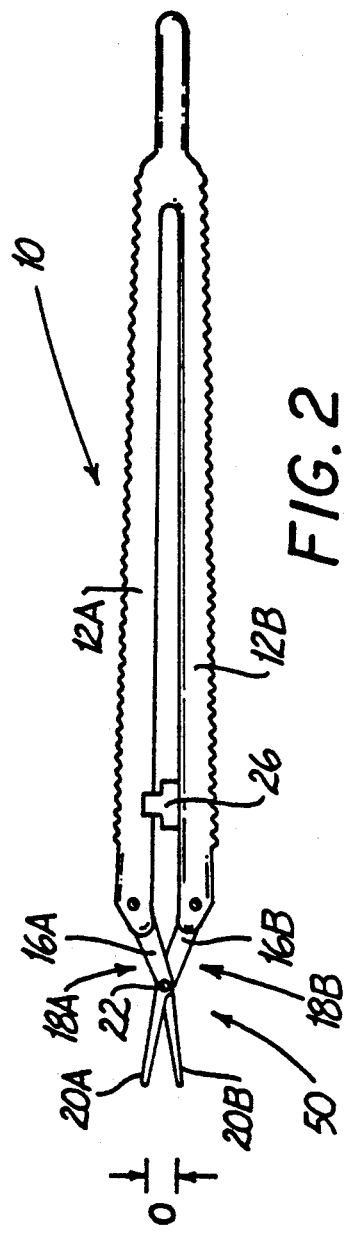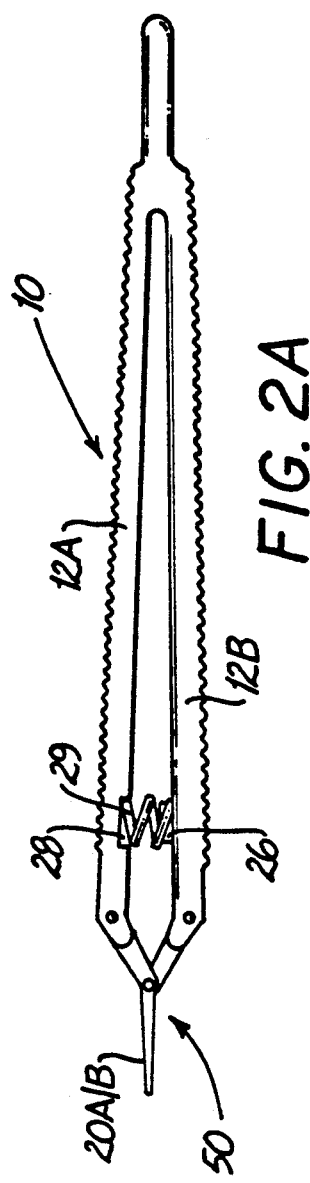

SURGICAL APPARATUS FOR REMOVING FASTENERS

FIELD OF THE INVENTION

The present invention relates to surgical fastener removers, and more particularly relates to surgical fastener removers adapted for use in removing vascular clips.

DISCUSSION OF THE PRIOR ART

In various surgical procedures, it is necessary to unite or reunite various parts of the anatomy. This anatomy may include small blood vessels, nerves and the like. The procedure of joining blood vessels is known as vascular anastomosis.

U.S. Pat. No. 4,586,503 issued to Kirsch, et al. discloses anastomosis using surgical clips. The Kirsch patent, which is incorporated herein by reference, also discloses a microvascular surgical clip comprising a pair of arcuate legs interconnected by a bridging section. The clip can be made of a biologically acceptable material which is capable of plastic deformation. A tweezer-type tool for holding and crimping the microclips is also disclosed. Kirsch, however, does not disclose a method or tool for removing the microclips.

Prior to the presently disclosed invention, these clips were removed by cutting the bridging section, or backspan, of the clip and subsequently removing the two leg portions from the body. A disadvantage of this procedure is that the two leg portions are quite small and can become difficult to find or even lost in the body cavity. It would therefore be advantageous to provide a clip or fastener remover which does not require cutting the backspan of these clips. Such a remover could also be utilized to facilitate removal of other types of clips or fasteners.

Various types of surgical fastener or staple removers are known in the art. For example, U.S. Pat. No. 4,589,631 discloses a surgical staple remover comprising two pivotally connected arms, each of which is made up of a proximal handle and a distal nose piece. The apparatus operates in a manner similar to a pair of pliers. In operation, the surgeon grasps a staple backspan with the nose piece of the remover and then squeezes the handles to bend the staple backspan to cause the staple legs to pull out of the body. This type of staple remover, however, is not suited for removal of various types of fasteners which do not have a backspan so readily accessible or deformable, i.e., such as the clips disclosed in Kirsch.

Therefore, the novel surgical apparatus pursuant to the present invention advantageously provides a surgical fastener remover capable of removing fasteners without the need for cutting or direct bending of the fastener backspan.

SUMMARY OF THE INVENTION

The present invention provides a novel surgical apparatus which is easy to manufacture and operate. The apparatus comprises means for contacting the legs of a fastener and means for moving the contacting means from a first position to a second position. The contacting and means comprises two fastener contacting members having proximal and distal ends. The two contacting members are configured and dimensioned to contact the inner portion of a fastener's legs. Controlled movement of the contacting members allows for a surgeon to force the legs open to a configuration suitable for removal from the body. A pair of elongated members are provided to manipulate the two contacting members, wherein the contacting members are secured to the elongated members (e.g., a single contacting member secured to each elongated member).

In order to access the inner portions of the fastener legs, the contacting members are in an overlying relationship when the apparatus is in a static state. The tips at the distal ends of the contacting members enhance accessibility to the fastener legs. After maneuvering the overlying contacting members under the backspan to a position between the fastener legs, the elongated members may then be forced together to cause the contacting member's legs to spread apart, thereby causing the fastener legs to open to a configuration suitable for removable. A stop member can be provided to limit the movement of the elongated members so that the distal ends of the contacting members, the ends which contact the fastener, do not open past a predetermined distance. This ensures that the clip is not hyper extended and, therefore, further ensures that the clip does not break.

DESCRIPTION OF THE DRAWINGS

The foregoing objects and other features of the invention will become more readily apparent and may be understood by referring to the following detailed description of illustrative embodiments of the surgical apparatus for removing fasteners, taken in conjunction with the accompanying drawings, in which:

FIG. 1 illustrates a top view of a first embodiment of the present invention wherein the two elongated members are resiliently biased apart;

FIG. 2 illustrates the apparatus of FIG. 1 wherein the elongated members are forced together;

FIG. 2A illustrates an alternate embodiment of the present invention having a spring member disposed between the elongated members;

DETAILED DESCRIPTION OF THE PREFERRED EMBODIMENTS

Figure 3:
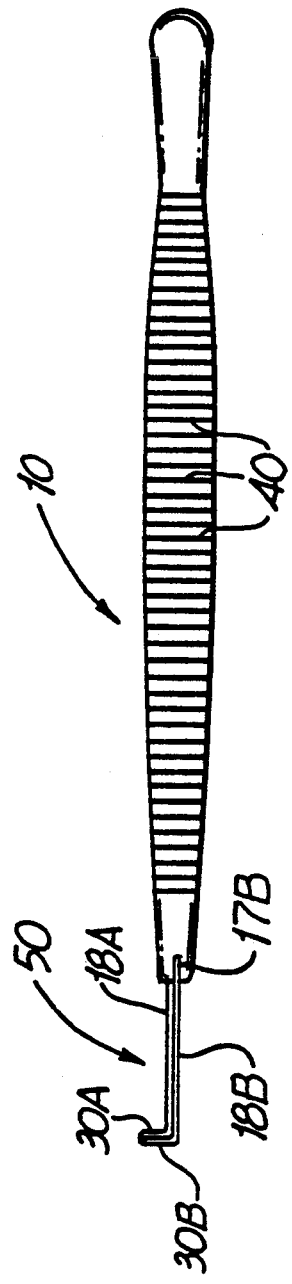
FIG. 3 illustrates a side view of the apparatus of FIG. 1.

Referring now in specific detail to the drawings, in which like reference numerals identify similar or identical elements, FIG. 1 illustrates a first embodiment of the surgical apparatus 10 for removing surgical fasteners. Apparatus 10 comprises two elongated members 12A and 12B which converge and join at end portion 14. The elongated members join at end portion 14 in such a manner so that members 12A and 12B are at least partially resiliently biased apart when the apparatus is in a static state. Both elongated members 12A and 12B and end portion 14 can be machined from a common piece of resilient material. Suitable materials for these portions can include, for example, glass-filled nylon or acrylonitrile butadiene styrene (ABS). Preferably, 30% glass-filled nylon is used.

Turning to the clip contacting portion 50 of apparatus 10, and with reference to FIGS. 1 and 2, clip contacting members 18A and 18B have proximal portions 16A and 16B and distal portions 20A and 20B. Proximal portions 16A and 16B are disposed in recesses 17A and 17B, respectively (see FIGS. 3 and 4), of elongated members 12A and 12B, and secured thereto by pivot pins 24A and 24B respectively. Alternatively, the elongated members may be formed integrally with the contacting members. Fastener contacting members 18A and 18B are secured to each other by pin 22 which also defines a common pivot point. Contacting members 18A and 18B are configured and positioned such that distal portions 20A and 20B are in an overlying relationship (20A overlying 20B in FIG. 1) when elongated members 12A and 12B are in their static, resiliently biased apart state. Squeezing 12A and 12B together forces proximal portions 16A and 16B together, causing 18A and 18B to pivot about pin 22, causing distal portions 20A and 20B to move apart.

Figure 3A:
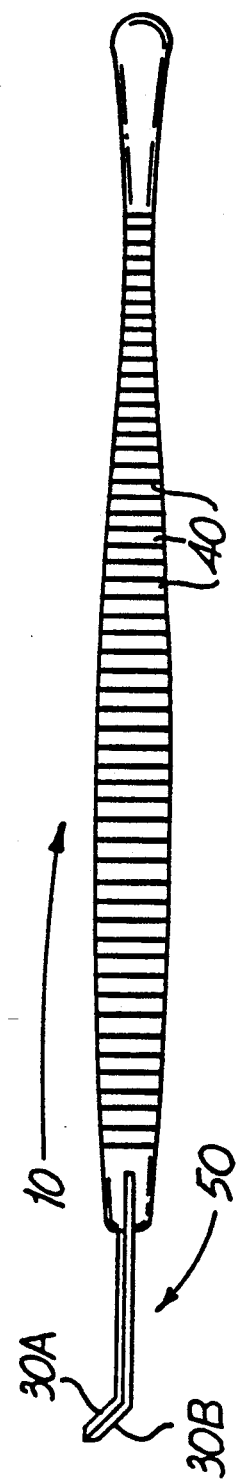
FIG. 3A illustrates another alternate embodiment of the present invention.

Fastener contacting members 18A and 18B terminate in tips 30A and 30B, best shown in FIGS. 3 and 3A. In FIG. 3, tips 30A and 30B are angled 90 degrees from the horizontal plane of apparatus 10. In an alternate embodiment, shown in FIG. 3A, tips 30A' and 30B' are at a different angle and tapered. The angling and tapering of the tips may be modified to meet the particular dimensions of the fastener to be removed.

Elongated members 12A and 12B can have an irregular surface to facilitate grasping during use. For example, as illustrated in FIG. 3, ridges 40 may be provided along the outer surface of elongated members 12A and 12B.

The apparatus 10, as shown in FIGS. 1 and 2, includes a stop member 26, positioned on elongated member 12B, which extends towards elongated member 12A. When elongated members 12A and 12B are forced together, stop member 26 contacts elongated member 12A at recess 28, thereby preventing further movement of the elongated members. This in turn prevents distal portions 20A and 20B of the contacting members 18A and 18B from moving further apart. As can be seen, stop member 26 provides a mechanism to control the degree of movement of tips 30A and 30B. By controlling the spread between tips 30A and 30B, indicated by D of FIG. 2, it is possible to prevent hyper extension and/or breakage of the fastener to be removed. Additionally, by controlling the movement of the contacting members, the fastener remover of this invention can be adapted to remove fasteners of various size, configuration, and composition.

Figure 4:
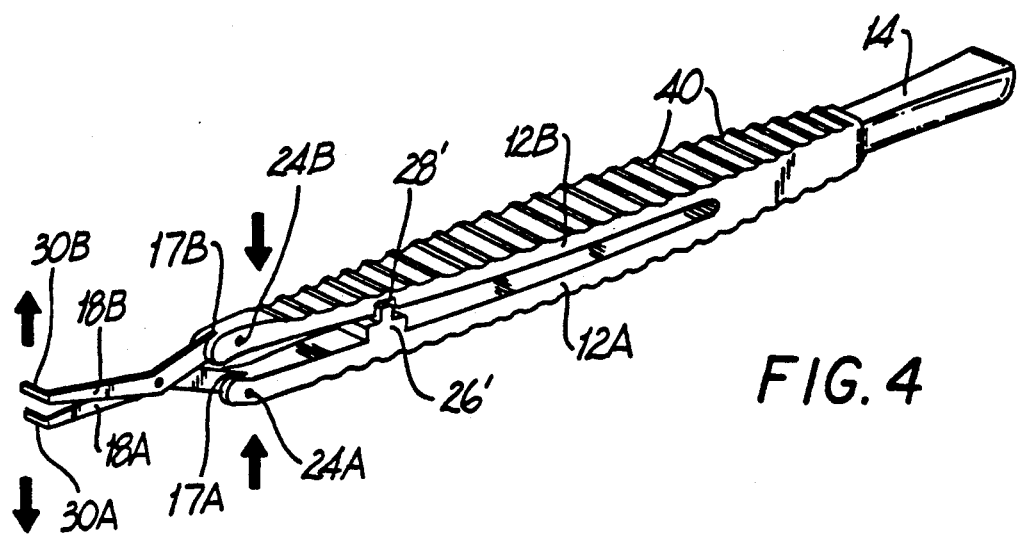
FIG. 4 illustrates a side perspective view of FIG. 1.

Stop member 26 and recess 28 may assume various alternative configurations. In FIGS. 1 and 2, stop member 26 and recess 28 are cylindrical. An alternative configuration, as shown in FIGS. 4 and 5, stop member 26' and recess 28' are rectangular in configuration.

FIG. 2A illustrates an alternative, preferred embodiment, wherein stop member 26 and recess 28 may also have a spring member 29 disposed thereon and therein, respectively (see FIG. 2A). Spring member 29 can serve at least three purposes. First, it can at least partially bias apart elongated members 12A and 12B. Second, this spring biasing can obviate the need for constructing elongated members 12A and 12B from resilient material. Third, it can also serve to control the degree of movement of distal portions 20A and 20B of fastener contacting members 18A and 18B, in a manner similar to stop member 26, as described above.

Figure 5:
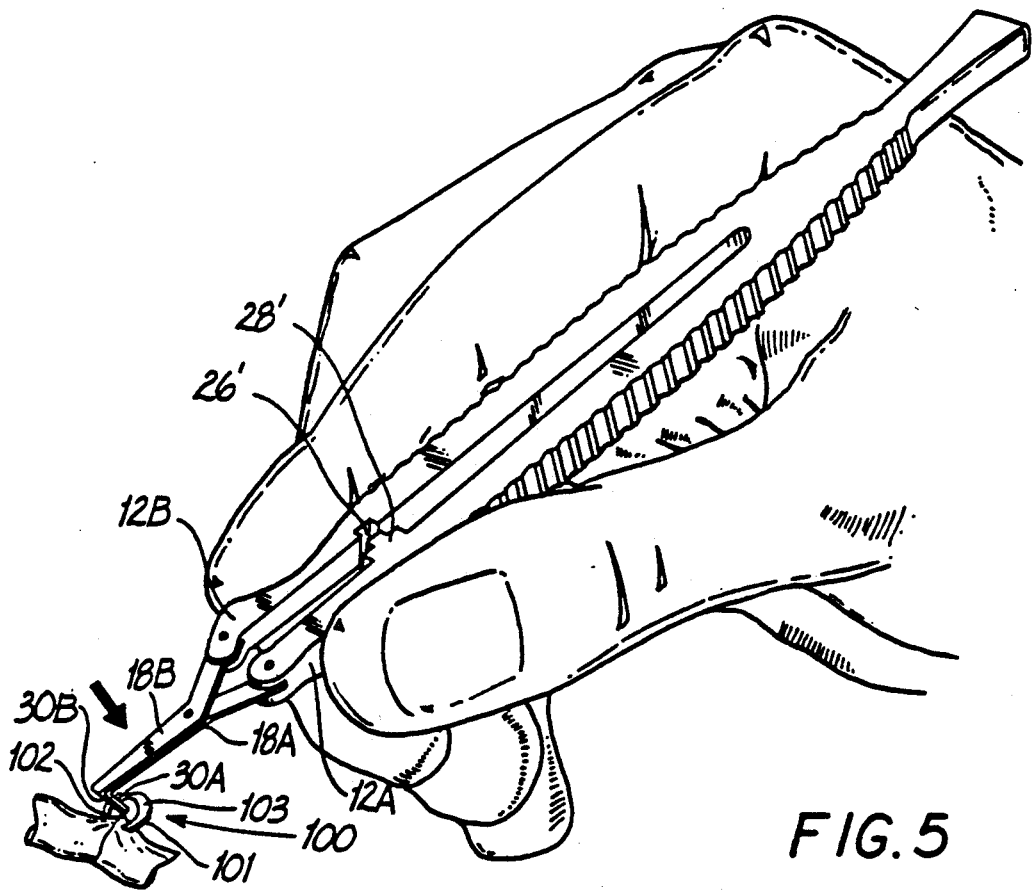
FIG. 5 illustrates a side perspective view of the apparatus of FIG. 1 showing the fastener contacting members approaching a clip to be removed.
Figure 6:
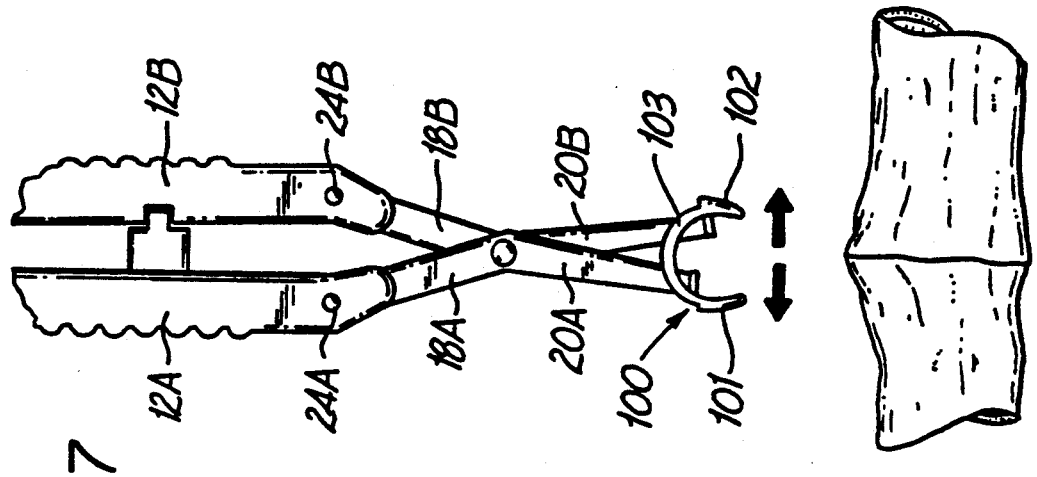
FIG. 6 illustrates a top view of the apparatus of FIG. 1 showing the fastener contacting members contacting a clip.
Figure 7:
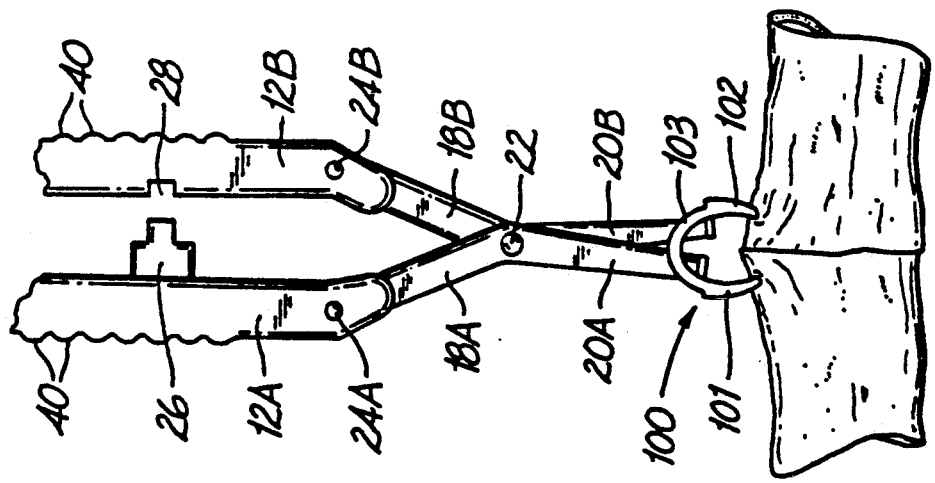
FIG. 7 illustrates the apparatus of FIG. 1 after the clip has been removed.

In operation, and turning to FIG. 5, a side perspective view of the fastening removing apparatus 10 of the present invention is shown approaching a clip 100 of the type disclosed in U.S. Pat. No. 4,586,503, incorporated herein by reference, to be removed. Specifically 30A and 30B of fastener contacting members 18A and 18B are positioned under backspan 103 to contact and press against the inner portions of legs 101 and 102 of clip 100. FIGS. 6 and 7 represent a top view of a preferred embodiment of the fastener contacting members 18A and 18B and their securement to elongated members 12A and 12B, respectively. Clip 100 is removed by forcing elongated members 12A and 12B together, thereby spreading tips 30A and 30B apart to contact and force legs 101 and 102 of clip 100 apart (FIG. 6). The more 12A and 12B are squeezed the more 30A and 30B spread and the further the clip legs are spread. FIG. 7 illustrates clip 100 sufficiently open for removal, wherein elongated members 12A and 12B of apparatus 10 have traveled to a point where stop member 26 has contacted recess 28. As a result of stop member 26 preventing further travel of tips 30A and 30B, the distance between tips 30A and 30B are such that clip 100 is not hyper extended. Clip 100 may then be lifted from the body cavity, removed from the apparatus and discarded. The apparatus may then be used to remove other clips from the body.

While the invention has been particularly shown and described with reference to the preferred embodiments, it will be understood by those skilled in the art that various modifications in form and detail may be made therein without departing from the scope and spirit of the invention. Accordingly, such modifications are to be considered within the scope of the invention as defined by the claims.

What is claimed is:

1. A surgical apparatus for removing from the body a fastener having a pair of legs joined by a backspan, the apparatus comprising:

first and second elongated members having proximal and distal ends;

first and second contacting members having proximal and distal end portions, said first contacting member proximal end portion being pivotally pinned to said first elongated member distal end and said second contacting member proximal end portion being pivotally pinned to said second elongated member distal end; and a pin passing through each said contacting members, said pin defining a common pivot point for said contacting members, wherein when said elongated members are forced towards each other, the proximal end portions of said contacting members are caused to move towards each other and the distal end portions of said contacting members are caused to move away from each other.

2. An apparatus according to claim 1, wherein each of said contacting members further comprise an angled tip portion disposed on said distal end portions.

3. An apparatus according to claim 2, wherein said tip portion is angled from the horizontal plane of said apparatus.

4. An apparatus according to claim 3, wherein said tip portion is angled about 90° from the horizontal plane of said apparatus.

5. An apparatus according to claim 2, wherein said tip portion is tapered.

6. An apparatus according to claim 1, wherein said first and second elongated members converge towards their proximal ends and terminate in a single end portion, thereby forming a pivot point.

7. An apparatus according to claim 6, wherein said first and second elongated members are resiliently biased apart.

8. An apparatus according to claim 6, wherein said first and second elongated members are at least partially biased apart by a spring disposed therebetween.

9. An apparatus according to claim 6, further comprising means for limiting the movement of said contacting members.

10. An apparatus according to claim 9, wherein said limiting means comprises at least one stop member positioned on at least one of said elongated members and extending towards said other elongated member.

11. An apparatus according to claim 10, wherein when said elongated members are forced together, said at least one stop member contacts the opposing elongated member to limit movement thereof.

12. An apparatus according to claim 11, wherein said opposing elongated member has at least one recess configured and dimensioned to permit said at least one stop member to at least partially enter therein when said elongated members are forced together.

13. An apparatus according to claim 9, wherein said limiting means comprises at least one spring disposed between said elongated members.

14. An apparatus according to claim 13, wherein said opposing elongated member has at least one recess, said at least one recess being configured and dimensioned to permit said at least one spring to at least partially enter therein.

15. An apparatus according to claim 13, further comprising a stop member positioned on at least one of said elongated members and extending towards said other elongated member, wherein said at least one spring is disposed about said stop member.

16. A surgical apparatus for removing from the body a fastener having a pair of legs joined by a backspan, the apparatus comprising:
   a pair of contacting members having proximal and distal end portions, each said contacting members having an angled body portion disposed between said proximal and distal end portions;
   a pin passing through each said contacting member angled body portion, said pin defining a common pivot point for said contacting members, wherein said distal end portions of said contacting members are disposed in an overlying relationship distal of said pin; and
   first and second elongated members having proximal and distal ends, wherein one of said contacting members is pivotally secured to the distal end of said first elongated member and the other contacting member is pivotally secured to the distal end of said second elongated member.

17. An apparatus according to claim 16, wherein said first and second elongated members converge towards their proximal ends and terminate in a single body portion and wherein said first and second elongated members are resiliently biased apart.

18. An apparatus according to claim 16, wherein when said elongated members are forced towards each other, the distal end portions of said contacting members are caused to move away from each other.

19. An apparatus according to claim 16, further comprising means for limiting the movement of said contacting members when said elongated members are forced towards each other.

20. An apparatus according to claim 16, wherein said elongated members further comprise an irregular surface formed in an outer surface of said elongated members to facilitate grasping of said apparatus during use.

21. An apparatus according to claim 20, wherein said irregular surface comprises a ridged surface.

22. A method of removing a surgical fastener having a pair of legs joined by a backspan comprising:
   a) providing an apparatus comprising two fastener contacting members configured and dimensioned to contact said fastener legs, said contacting members being pivotally pinned to two biased apart elongated members, said elongated members providing means for moving said contacting members from a first position, wherein the distal ends of said contacting members are disposed in an overlying relationship, to a second position, wherein the distal ends of said contacting members are at least partially spaced apart;
   b) positioning said apparatus such that said contacting members are located between said fastener legs; and
   c) forcing together said elongated members to cause said contacting members to move from said first position to said second position, further causing said fastener legs to spread to a configuration suitable for removal from the body.

23. The method according to claim 22, wherein the step of providing said apparatus further comprises providing elongated members which are resiliently biased apart.

24. The method according to claim 22, wherein the step of providing said apparatus further comprises providing a spring member disposed between said elongated members.

25. The method according to claim 22, wherein the step of providing said apparatus further comprises providing means for limiting the movement of said contacting members.

26. The method according to claim 25, wherein the step of providing said limiting means further comprises providing at least one stop member further comprises providing at least one stop member positioned on at least one of said elongated members and extending towards the other elongated member.

27. A surgical apparatus for removing from the body a fastener having a pair of legs joined by a backspan, the apparatus comprising:
   first and second elongated members having proximal and distal ends, each said elongated member proximal ends converging and terminating in a single end portion to form a common pivot point, each said elongated member distal ends being resiliently spaced apart;
   first and second contacting members having proximal and distal end portions, said first contacting member proximal end portion being secured to said first elongated member distal end and said second contacting member proximal end portion being secured to said second elongated member distal end; and at least one pin passing through each said contacting members, said pin defining a common pivot point for said contacting members.

28. An apparatus according to claim 27, wherein when said elongated member distal ends are forced towards each other, the proximal end portions of said contacting members are caused to move towards each other and the distal end portions of said contacting members are caused to move away from each other.

* * * * *